United States Patent [19]

Bagli et al.

[11] Patent Number: 4,469,693
[45] Date of Patent: Sep. 4, 1984

[54] 2-(4-SUBSTITUTED ALKYL-1-PIPERAZINYL)-2,4,6-CYCLOHEPTATRIEN-1-ONE DERIVATIVES

[75] Inventors: Jehan F. Bagli, Kirkland; Tibor Bögri, Montreal; Katherine Voith, Dorval, all of Canada

[73] Assignee: Ayerst, McKenna & Harrison Inc., Montreal, Canada

[21] Appl. No.: 124,163

[22] Filed: Feb. 25, 1980

[51] Int. Cl.$^3$ .................. A61K 31/495; C07D 241/04
[52] U.S. Cl. .................................... 424/250; 544/121; 544/360; 544/362; 544/370; 544/373; 544/398; 544/399; 544/400; 544/402
[58] Field of Search ................ 424/250; 544/370, 373, 544/399, 398, 400, 402

[56] References Cited

PUBLICATIONS

Sianesi, et al., "J. Med. Chem.", vol. 10, 1967, pp. 1144–1148.
Biggi, et al., "J. Amer. Chem. Soc.", vol. 94, 1972, pp. 4700–4707.
Toda, et al., "Chemical Abstracts", vol. 76, 1972, Col. 72185f.
Biggi, et al., "J. Amer. Chem. Soc.", vol. 95, 1973, pp. 7101–7107.
Veracini, et al., "J. Amer. Chem. Soc. Commun.", 1977, pp. 623–624.
Abadir, et al., "J. Chem. Soc.", 1952, pp. 2350–2353.
Nozoe, et al., "Chemical Abstracts," vol. 70, 1969, Col. 87244z.

Primary Examiner—Donald G. Daus
Assistant Examiner—James H. Turnipseed
Attorney, Agent, or Firm—Arthur E. Wilfond

[57] ABSTRACT 2-(4-Substituted alkyl-1-piperazinyl)-2,4,6-cycloheptatrien-1-one derivatives, therapeutically acceptable acid addition salts thereof, processes for their preparation, methods of using the derivatives and pharmaceutical compositions of the derivatives are disclosed. The derivatives exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

29 Claims, No Drawings

2-(4-SUBSTITUTED ALKYL-1-PIPERAZINYL)-2,4,6-CYCLOHEPTATRIEN-1-ONE DERIVATIVES

BACKGROUND OF THE INVENTION

This invention relates to novel 2-(1-piperazinyl)-2,4,6-cycloheptatrien-1-one derivatives, to therapeutically acceptable acid addition salts thereof, to a process for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor stimulation.

The following references were obtained from a literature search for 2-substituted tropones: E. Sianesi et al., J. Med. Chem., 10, 1144 (1967); G. Biggi et al., J. Amer. Chem. Soc., 94, 4700 (1972); T. Toda et al., Chem. Abstr., 76, 72185f (1972) for Bull. Chem. Soc. Jap., 45, 226 (1972); G. Biggi et al., J. Amer. Chem. Soc., 95, 7101 (1973); C. A. Veracini et al., J. Chem. Soc. Commun., 623 (1974); B. J. Abadir et al., J. Chem. Soc., 2350 (1952) and T. Nozoe et al., Chem. Abstr., 70, 87244z (1969) for Bull. Chem. Soc. Jap., 41, 2978 (1968). These references disclose compounds which like the compounds of this invention are 2,4,6-cycloheptatrien-1-one derivatives. Of these 2,4,6-cycloheptatrien-1-one derivatives, the 2-piperidinyl-2,4,6-cycloheptatrien-1-one described by G. Biggi et al., J. Amer. Chem. Soc., 94, 4700 (1972), cited above, can be considered the most closely related to the compounds of this invention. However, the latter 2-piperidinyl derivative is treated as a chemical curiosity without any indicated useful pharmacological activity. Furthermore, the compounds of this invention differ from the compounds of Biggi et al., by having a 1-piperazinyl group at position 2 of the 2,4,6-cycloheptatrien-1-one ring.

SUMMARY OF THE INVENTION

The compounds of this invention are represented by formula I

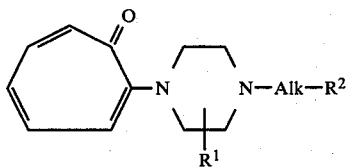

in which Alk is a divalent alkyl having one to six carbon atoms; $R^1$ is hydrogen or lower alkyl having one to three carbon atoms; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkyl, halo, lower alkoxy, hydroxy or trifluoromethyl, or phenoxy mono-, di- or trisubstituted with lower alkyl, halo, lower alkoxy, acetylamino, hydroxy or trifluoromethyl; or a therapeutically acceptable acid addition salt thereof.

A preferred group of compounds of this invention is represented by formula I in which Alk is a divalent alkyl having one to six carbon atoms; $R^1$ is hydrogen; and $R^2$ is lower alkoxy, cyano, aminocarbonyl, lower alkoxycarbonyl, cyclo(lower)alkyl, phenyl, phenoxy, hydroxy(lower)alkyl, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkoxy or hydroxy, or phenoxy mono-, di- or trisubstituted with lower alkyl, halo or acetylamino; or a therapeutically acceptable acid addition salt thereof.

A more preferred group of compounds of this invention is represented by formula I in which Alk is a divalent alkyl having one to three carbon atoms; $R^1$ is hydrogen; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono- or disubstituted with lower alkoxy or hydroxy, or phenoxy monosubstituted with lower alkyl, halo or acetylamino; or a therapeutically acceptable acid addition salt thereof.

A most preferred group of compounds of this invention is represented by formula I in which Alk is a divalent alkyl having one or two carbon atoms; $R^1$ is hydrogen; and $R^2$ is lower alkoxy, cyano, 1-oxo(lower)alkoxy, or phenyl mono- or disubstituted with lower alkoxy or hydroxy; or a therapeutically therapeutically acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 2-methylpropyl, pentyl, hexyl and the like, unless stated otherwise. 1-Methylethyl and 2-methylpropyl also are known as isopropyl and sec-butyl.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "1-oxo(lower)alkyl" or "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "halo" as used herein means halogens and includes fluorine.

The term "halo" as used herein means halogens and includes fluorine, chlorine, bromine and iodine, unless stated otherwise.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "—Alk—" as used herein means a divalent alkyl radical derived from a straight and branched chain aliphatic hydrocarbons containing from one to six carbon atoms by removal of two hydrogen atoms, unless stated otherwise, and includes, for example

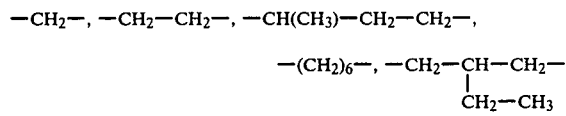

and the like.

The term "lower alkanol" as used herein means both straight and branched chain alkanols containing from one to four carbon atoms and includes methanol, ethanol, isopropanol, butanol and the like.

The term "organic proton acceptor" as used herein means the organic bases, or amines for instance, triethylamine, pyridine, N-ethyl-morpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impact slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960's of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in Parkinson's disease and certain neuroendocrine disorders, for example, hyperprolactinemia, galactorrhea, amenorrhea, impotence, hypertension and other central nervous system disorders.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367, 69–93 (1971) who, by means of unilateral injections of 6-hydroxydopamine (6-OHDA) into the DA pathway, could produce selective lesions of the ascending DA pathways on one side of the brain. Ungerstedt (1971) demonstrated in these lesioned rats that DA receptor agonists induced rotational behavior towards the innervated side. The response is due to the development of receptor supersensitivity in the denervated striatum resulting in a higher degree of DA receptor activity on the denervated—as compared to the innervated—side after treatment with DA receptor agonists. Due to this imbalance between the two sides, a rotational behavior is elicited, the direction being always towards the less activated side. It is of interest that in the discovery of the DA receptor stimulating properties of bromocriptine, the 6-OHDA rotational model was utilized [H. Corrodi et al., J. Pharm. Pharmacol., 25, 409–412 (1973)].

In the test for rotational behavior in rats following the unilateral 6-OHDA-induced destruction of one nigrostriatal pathway, the method described by C. J. Pycock and C. D. Marsden, Europ. J. Pharmacol., 47, 167 (1978) was followed. The rats (230–250 g) were anesthetized with sodium pentobarbital (40 mg/kg i.p.) and intracerebral injections were made using a Stoelting stereo-taxic instrument, (C. H. Stoelting Co., Chicago, Ill., U.S.A.). Unilateral injections of 6-OHDA hydrobromide (8 μl delivered at a rate of 1 μl per min) were made into the ascending forebrain bundle (MFB) in the lateral hypothalamus according to the coordinates of the De Groot brain atlas, J. De Groot, Verhandel, Koninkl. Ned. Akad. Wetenschap. Natuurk. 52; 1-40 (1959), (A: +4.6, L: ±1.9, V: −2.7). 6-OHDA was made up in ice-cold distilled water containing 0.2 mg/ml ascorbic acid.

Three weeks after operation, the rats were tested for rotational behavior in response to apomorphine hydrochloride (0.25 mg/kg, s.c.). Rats which consistently showed more than 5 turns/min after apomorphine were selected and the compound of formula I was then administered. The rat was immediately placed in the rotometer, described by K. Voith and J. R. Cummings, Can. J. Pharmacol., 54, 551 (1976), and the rotation was continuously recorded until drug effect subsided. By using this test, the compounds of formula I can be shown to be effective dopamine receptor agonists.

A recently developed animal model, described by G. P. Smith and R. C. Young in "Advances in Neurology", Vol. 5, F. H. McDowell and A. Barbeau, Eds., Raven Press, New York, pp. 427–432 (1974), shows that rats exhibit almost complete akinesia in an open field following the bilateral injection of 6-OHDA into the anterolateral hypothalamus. The troponylpiperazines of formula I are able to reverse this 6-OHDA-induced hypokinesia and as a result, function as dopamine receptor agonists. In this test for dopamine receptor agonists, the compounds of formula I exhibit a pharmacological response that is quantitatively comparable to that of apomophine and bromocriptine.

Experiments were performed on male Sprague-Dawley rats housed in air-conditioned quarters. The room was lighted between 0700 and 1900 hr daily and was maintained at a temperature of 24° C.±2° C.

The method of Smith and Young, cited above, was followed. Rats (approximately 280 g) were operated on under sodium pentobarbital anesthesia. Using a Stoelting stereotaxic instrument, the tip of a 26 gauge cannula was positioned in the anterolateral hypothalamus (7 mm anterior to the interaural line, 2 mm lateral to the midline and 8 mm below the dura) according to the De Groot brain atlas, noted above. Via a polyethylene tubing (PE 20) the cannula was connected to a 10 $\mu$l syringe which was mounted in a Starrett micrometer head drive, C. H. Stoelting Co., Chicago, Ill., U.S.A. All injections were bilateral. Each injection consisted of 4 $\mu$l of distilled water containing 6-OHDA (6.5 $\mu$g base/$\mu$l) and ascorbic acid (0.4 $\mu$g/$\mu$l).

The animals had free access to Purina Laboratory Chow pellets and tap water. However since anterolateral hypothalamic 6-OHDA injections produce aphagia and adipsia, intragastric feeding was necessary in order to prevent drastic weight loss. The rats received a daily gastric intubation of 2 g of the "modified rat tube feeding diet" (ICN Pharmaceuticals, Inc., Clevaland, Ohio, U.S.A.) mixed with approximately 2 ml tap water.

Ambulation in the open field was evaluated in an apparatus consisting of a wooden box (69 cm×69 cm×42 cm) with an arborite floor. The floor was divided into 36 squares (11.5 cm×11.5 cm). The placement of all four limbs in one square was taken as one ambulation score.

In the present experiments all compounds were evaluated four days after the intracerebral injection of 6-OHDA. The rat was placed into the center of the open field and observed for a 2-min period. Only rats with almost total akinesia were used. Apomorphine, bromocriptine or the compounds of formula I were injected s.c. to groups of 4–12 rats. Subsequently, the number of squares were counted which the animal entered during several 2-min observation periods. Apomorphine was evaluated at 5, 10, 15, 20 and 30 min; bromocriptine at 2, 3, 4, 5, 6 and 7 hr; and the compounds of formula I at 15, 30, 45, 60, 90 and 120 min after injection. Each animal was used only once. The results are expressed as cumulative number of ambulation scores which are the sums of the scores obtained during the 2-min observation periods.

The following substances were used; apomorphine hydrochloride (Macfarian Smith Ltd., Edinburgh, Scotland), bromocriptine (CB-154) (Sandoz Pharmaceuticals, East Hanover, N.J., U.S.A.) and 6-OHDA hydrobromide (Aldrich Chemical Co., Inc., Milwaukee, Wis.; U.S.A.). The compounds were dissolved in distilled water or suspended in distilled water with a few drops of polysorbate 80 (Tween 80; "Tween" is a registered trade mark). If the compound was an oil, 0.4 ml of dimethyl sulfoxide was added. Solutions were prepared fresh on the day of the experiment. The 6-OHDA solution was kept in ice throughout the injection procedure. All doses refer to the base.

Using the above described method, apomorphine at a dose of 0.5 mg/kg exhibited a score of 135±41 and bromocriptine at a dose of 10 mg/kg exhibited a score of 112±23. Similarly, the following representative compounds of formula I are effective dopamine receptor agonists (the amount of the compound and its cumulative ambulation score are indicated in the parentheses): 4-(2-oxo-3,5,7-cycloheptatrien-1-yl)-1-piperazine-acetonitrile (described in Example 3, at a dose of 50 mg/kg exhibited a score of 126±51), 2-[4-(2-ethoxyethyl)-1-piperazinyl]-2,4,6-cycloheptatrien-1-one (described in Example 3, at a dose of 50 mg/kg exhibited a score of 67±16), 2-[4-[2-(3,4-dimethoxyphenyl)ethyl]-1-piperazinyl]-2,4,6-cycloheptatrien-1-one (described in Example 4, at a dose of 10 mg/kg exhibited a score of 101±28), 2-[4-[2-(3,4-dihydroxyphenyl)ethyl]-1-piperazinyl]-2,4,6-cycloheptatrien-1-one (described in Example 5, at a dose of 25 mg/kg exhibited a score of 98±57), 4-(2-oxo-3,5,7-cycloheptatrien-1-yl)-1-piperazine-acetamide (described in Example 6, at a dose of 50 mg/kg exhibited a score of 42±14), 2-[4-[2-(acetyloxy)ethyl]-1-piperazinyl]-2,4,6-cycloheptatrien-1-one (described in Example 7, at a dose of 50 mg/kg exhibited a score of 232±54), and 2,2-dimethylpropanoic acid, 2-[4-(2-oxo-3,5,7-cycloheptatrien-1-yl)-1-piperazinyl]ethyl ester (described in Example 8, at a dose of 50 mg/kg exhibited a score of 137±29).

The above described test method for dopamine receptor agonists shows that the compounds of formula I are active as dopamine receptor agonists. The compounds, thus, can be used clinically in the treatment of hyperprolactinemia, galactorrhoea, amenorrhoea, impotence, diabetes, Parkinsonism, acromegaly, hypertension and other central nervous system disorders which respond to dopaminereceptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacutre of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aforementioned variations will occur. However a dosage level that is in the range of from about 1.0 to about 100 mg per kilogram body weight per day in single or divided doses is employed most desirably for i.p. administration in order to achieve effective results. For oral administration, effective amounts can range from about 1.0 to about 250 mg per kilogram body weight per day in single or divided doses preferably about 5.0 to 100 mg per kilogram body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and its derivatives, dopaminergic ergot derivatives, especially bromocriptine and iergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-prolyl-N-methyl-D-leucylglycinamide (pareptide), biperiden, cycrimine hydrochloride, procyclidine, trihexyphenidyl hydrochloride, benztropine mesylate, chlorphenoxamine hydrochloride, diphenhydramine hydrochloride, orphenadrine hydrochloride, ethopropazine hydrochloride and the enzymes, monoamine oxidase B and catechol-O-methyl transferase. A combination of the foregoing agents can be substituted for a single agent. Suitable methods of administration, compositions and dosages of the agents are well known in the art; for instance, "Physican Desk Reference", 32 ed., Medical Economics Co., Oradell, N.J., U.S.A., 1978. When used in combination, the compound of formula I, or its therapeutically acceptable salt, is administered as described previously.

PROCESS

Reaction scheme 1 illustrates methods for preparing a number of the compounds of formula I.

REACTION SCHEME I

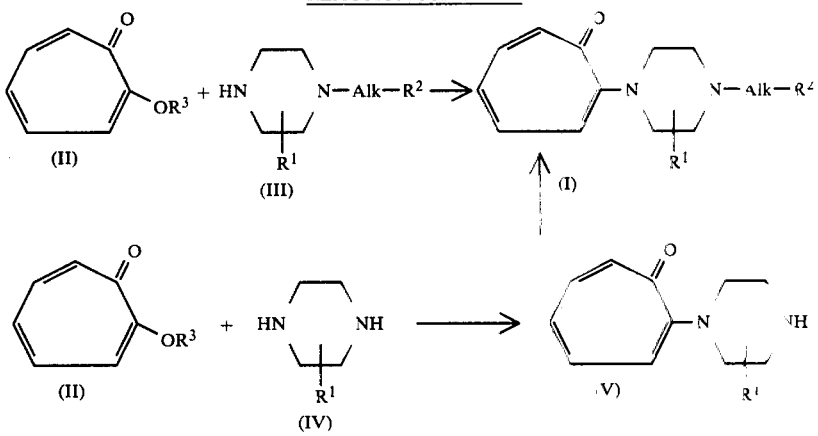

The 2-alkoxy-tropones, of formula II in which $R^3$ is lower alkyl, suitable as starting materials are described in a number of reports; for example, see the review on tropone derivatives, their preparation and their interconversions by F. Pietra, Chem. Rev., 73, 293 (1973). Thus, the 2-alkoxy-tropones are either known or they can be prepared by conventional means.

Also, the piperazine and piperazine derivatives of formulae III and IV are either known, commercially available or can be prepared by conventional means. For example, one useful method of preparing a compound of formula III, the appropriate nitrogen of the piperazine of formula IV wherein $R^1$ is as defined herein is first protected with an amino protecting group, for instance, benzyl, formyl, tert-butoxycarbonyl and the like. The desired Alk-$R^2$ group is then introduced onto the other nitrogen of this protected piperazine, various methods of introducing this group are described hereinafter. Subsequent removal of the protecting group, for example, hydrogenation in the case of benzyl, gives the corresponding piperazine derivative of formula III.

With reference to reaction scheme 1, the 2-alkoxy-tropone of formula II in which $R^3$ is lower alkyl, preferably methyl or ethyl, is condensed with the piperazine derivative of formula III in which Alk is a divalent alkyl having one to six carbon atoms; $R^1$ is hydrogen or lower alkyl having one to three carbon atoms; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkyl, halo, lower alkoxy, hydroxy or trifluoromethyl, or phenoxy mono-, di- or trisubstituted with lower alkyl, halo, lower alkoxy, acetylamino, hydroxy or trifluoromethyl to obtain the corresponding compound of formula I in which Alk, $R^1$ and $R^2$ are as defined herein. The condensation is readily effected by heating a solution of the compound of formula II with one to five, preferably 1.3 to 2.0, molar equivalents of the piperazine of formula III in an inert organic solvent, for example, a lower alkanol, benzene, chloroform, acetonitrile, toluene and the like, preferably methanol or ethanol, at 50° to 100° C. for 10 to 60 hours and isolating the corresponding compound of formula I.

By using the above condensation conditions, condensation of the compound of formula II with about one-half molar equivalent an 1-[amino(lower)alkyl]piperazine gives the corresponding compound of formula I in which $R^1$ is as defined herein and $R^2$ is 1-oxo-2,4,6-cycloheptatrien-2-ylamino.

The above described condensation of the compounds of formula II and formula III is especially useful for preparing the compounds of formula I in which $R^1$ is as defined herein and $R^2$ is phenyl or 1-oxo-2,4,6-cycloheptatrien-2-ylamino.

Condensation of the compound of formula II and the piperazine of formula IV, in the same manner as described above for the compounds of formulae II and III, gives the corresponding compound of formula V in which $R^1$ is as defined herein. The compound of formula V is condensed in the presence of a proton acceptor with a halide of formula X—Alk—$R^2$ wherein X is bromo, chloro or iodo; Alk is a divalent alkyl having one to six carbon atoms; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkyl, halo, lower alkoxy, hydroxy or trifluoromethyl, or phenoxy, mono-, di- or trisubstituted with lower alkyl, halo, lower alkoxy, acetylamino, hydroxy or trifluoromethyl to obtain the corresponding compound of formula I in which Alk, $R^1$ and $R^2$ are as defined herein. About one to ten, preferably 1.0 to 1. molar equivalents of the proton acceptor and about one to five, preferably 1.0 to 1.5, molar equivalents of the halide of formula X—Alk—$R^2$ are used. For this condensation, suitable proton acceptors can be selected from organic and inorganic proton acceptors, for example triethylamine, pyridine, N-ethylmorpholine, sodium bicarbonate, sodium or potassium carbonate, sodium or potassium lower alkoxide and the like. Sodium or potassium carbonate is the preferred proton acceptor. Usually the condensation is conducted in an inert organic solvent, for example, benzene, toluene, dichloromethane, chloroform, lower alkanol, acetonitrile, dimethylformide, acetone and the like. Acetonitrile and/or methanol is the preferred solvent for this condensation. To achieve the condensation, the reaction mixture is maintained at 20° to 85° C. for three hours to three days and the compound of formula I is isolated.

Another useful condensation involves the reaction of the compound of formula V in which $R^1$ is as defined herein with about one molar equivalent of a tosylate of formula TsO—Alk—$R^2$ wherein Alk is as defined herein $R^2$ is phenyl, phenoxy, phenyl mono-, di- or trisubstituted with lower alkyl, halo, lower alkoxy or trifluoromethyl, or phenoxy mono-, di- or trisubstituted with lower alkyl, halo, lower alkoxy, acetylamino or trifluoromethyl to obtain the corresponding compound of formula I in which Alk and $R^1$ are as defined herein and $R^2$ is as defined immediately above. This condensation requires the presence of about two molar equivalents of a proton acceptor, preferably sodium or potassium carbonate. An especially useful solvent for this condensation is acetone. The reaction mixture is maintained at about 50° to 60° C. for about 15 to 40 hours to obtain the corresponding compound of formula I.

Treatment of the above described compound of formula I in which Alk and $R^1$ are as defined herein and $R^2$ is phenyl mono-, di- or trisubstituted with lower alkoxy with about four to ten molar equivalents of boron tribromide in an inert organic solvent, preferably dichloromethane, at 10° to 30° C. for about two to ten hours gives the corresponding compound of formula I in which Alk and $R^1$ are as defined herein and $R^2$ is phenyl mono-, di- or trisubstituted with hydroxy.

The reaction of the above described compound of formula I in which Alk and $R^1$ are as described herein and $R^2$ is cyano with five to twenty molar equivalents of concentrated sulfuric acid at 10° to 30° C. for about two to five days, followed by treatment with a mixture of ice and concentrated ammonium hydroxide until the reaction is alkaline, gives the corresponding compound of formula I in which Alk and $R^1$ are as defined herein and $R^2$ is aminocarbonyl.

Intermediates of formula VI in which Alk and $R^1$ are as defined herein

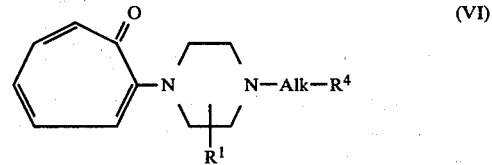 (VI)

and $R^4$ is hydroxy or chloro are also useful for preparing some compounds of formula I. A compound of formula VI in which Alk and $R^1$ are as defined herein and $R^4$ is hydroxy is prepared by condensing a compound of formula II in which $R^3$ is as defined herein with a 1-[hydroxy(lower)alkyl]-piperazine, in the same manner as described above for the condensation of the compounds of formulae II and III.

Acylation of the compound of formula VI in which Alk and $R^1$ are as defined herein and $R^4$ is hydroxy gives the corresponding compound of formula I in which Alk and $R^1$ are as defined herein and $R^2$ is 1-oxo(lower)alkoxy. The acylation is achieved by reacting the latter compound of formula VI with about an equimolar amount of a lower alkanoyl bromide or chloride and an organic proton acceptor, preferably triethylamine or pyridine, in an inert organic solvent, preferably benzene or dichloromethane, at 0° to 20° C. for one to three days, or with an excess of a lower alkanoic anhydride in the presence of an organic proton acceptor. When this acylation involves acetylation, a preferred method of acetylation is the reaction of the compound of formula VI with about 5 to 20 molar equivalents each of acetic anhydride and pyridine at 20° to 50° C. for 10 to 30 hours to obtain the corresponding compound of formula I in which Alk and $R^1$ are as defined herein and $R^2$ is acetyloxy.

Reaction of the compound of formula VI in which Alk and $R^1$ are as defined herein and $R^4$ is hydroxy with about two to three molar equivalents of thionyl chloride in an inert organic solvent, preferably chloroform, at about 10° to 30° C. for about 10 to 40 hours gives the corresponding intermediate of formula VI in which Alk and $R^1$ are as defined herein and $R^4$ is chloro.

Reaction of the compound of formula VI in which Alk and $R^1$ are as defined herein and $R^4$ is chloro with about an equimolar amount of thiourea in a solution of ethanol at about 70° to 80° C. for about one to five hours gives the corresponding intermediate having an [(aminoiminomethyl)amino]thio group. Acetylation of this intermediate with an excess of acetic anhydride, about 50 to 20 molar equivalents, at about 40° to 80° C. for about 30 minutes to five hours gives the corresponding compound of formula I in which Alk and $R^1$ are as defined herein and $R^2$ is acetylthio.

The following examples illustrate further this invention.

EXAMPLE 1

2-[4-(Phenylmethyl)-1-piperazinyl]-2,4,6-cycloheptatrien-1-one (I: Alk=$CH_2$, $R^1$=H and $R^2$=phenyl)

A mixture of 1-(phenylmethyl)-piperazine (3.2 g) and 2-methoxy-2,4,6-cycloheptatrien-1-one (1.6 g) in methanol (6 ml) was refluxed for 10 hr and evaporated. The residue was dissolved in a mixture of chloroform and water. The organic phase was separated, dried and evaporated. The residue was chromatographed on silica gel (200 g) using methanol-chloroform (5:95). The eluates were evaporated to give the title compound (2.7 g): mp 78°-80° C.; ir($CHCl_3$) 2400, 1705, 1620, 1350 and 1570 $cm^{-1}$; uv max(MeOH) 343 ($\epsilon$=9440) and 250 nm ($\epsilon$=14975); nmr($CDCl_3$) $\delta$2.9 (s, 3H), 3.5 (m, 8H), 6.27 (s, 2H), 7.0 (m, 5H) and 14.5 (broad, 2H); and Anal. Calcd for $C_{18}H_{20}N_2O_2$: C, 77.11% H, 7.19% N, 9.99% and Found: C, 77.08% H, 7.17% N, 9.74%.

In the same manner, but replacing 1-(phenylmethyl)-piperazine with an equivalent amount of N-(2-oxo-2,4,6-cycloheptatrien-1-yl)-1-piperazinylethanamine, the following compound of formula I was obtained:N,4-bis-(2-oxo-3,5,7-cycloheptatrien-1-yl)-1-piperazine-ethanamine (I: $R^1$=H, Alk=$CH_2CH_2$ and $R^2$=1-oxo-2,4,6-cycloheptatrien-2-ylamino): mp 130°-132° C. (crystallized from ethyl acetate); ir($CHCl_3$) 3300 and 1555 $cm^{-1}$; uv max(MeOH) 340 ($\epsilon$=22740) and 248 nm ($\epsilon$=40,285); nmr($CDCl_3$) $\delta$2.8 (m, 6H), 3.4 (m, 6H), 6.9 (m, 10H) and 7.6 (broad, 1H); and Anal. Calcd for $C_{20}H_{23}N_3O_2$: C, 71.19% H, 6.87% N, 12.45% and Found: C, 71.60% H, 7.09% N, 12.40%.

EXAMPLE 2

2-(1-Piperazinyl)-2,4,6-cycloheptatrien-1-one (V: $R^1$=H)

A solution of 2-methoxy-2,4,6-cycloheptatrien-1-one (136 g) and piperazine (136 g) in methanol (250 ml) was refluxed for 4 hr and the reaction vessel was placed in an ice bath. Water (150 ml), then acetic acid was slowly added until the solution was acidic. The mixture was filtered and the filtrate was evaporated and chromatographed on silica gel using chloroform-acetone (1:1) and then with acetic acid-methanol(1:4). The eluates from the latter solvent were evaporated to give an oil of the acetate salt (153 g) of the title compound.

Alternatively, the reaction solution was cooled to induce crystallization of the dimer and filtered. The filtrate was diluted with acetone to 1000 ml and a solution of methane sulfonic acid (106 g) in acetone (250 ml) was added to the filtrate in an ice bath. The precipitate was collected and washed with acetone and diethyl ether to give 146 g of the methane sulfonate salt of the title compound: mp 174°-176° C.; ir(mull) 2900, 1563 and 1180 $cm^{-1}$; uv max(MeOH) 343 ($\epsilon$=8910), 252 ($\epsilon$=13110) and 223 nm($\epsilon$=11250); nmr(DMSO-$d_6$)$\delta$2.35 (s, 3H), 3.35 (m, 8H), 6.95 (m, 5H) and 8.8 (broad, 2H); and Anal. Calcd for $C_{11}H_{14}N_2O$.$CH_3SO_3H$: C, 50.32% H, 6.33% N, 9.80% and Found: C, 50.06% H, 6.39% N, 9.44%.

EXAMPLE 3

4-(2-Oxo-3,5,7-cycloheptatrien-1-yl)-1-piperazineacetonitrile (I: Alk=$CH_2$, $R^1$=H and $R^2$=cyano)

A mixture of 2-(1-piperazinyl)-2,4,6-cycloheptatrien-1-one acetate (10.0 g, described in Example 2), chloroacetonitrile (13.2 g) and potassium carbonate (14.5 g) in acetonitrile (110 ml) was stirred at room temperature for 16 hr, and filtered. The filtrate was evaporated. The residue was chromatographed on silica gel (300 g) using ethyl acetate-acetone (4:1) give 1.9 g of the title compound, which was then crystallized from acetone-diethyl ether: mp 133°-135° C.; ir($CHCl_3$) 2230 and 1565 $cm^{-1}$; uv max(MeOH) 350 ($\epsilon$=9810), 254 ($\epsilon$=14575) and 222 nm($\epsilon$=11960); nmr($CDCl_3$) $\delta$2.75 (t, 4H), 3.4 (t, 4H), 3.55 (s, 2H) and 7.0 (m, 5H); and Anal. Calcd for $C_{13}H_{15}N_3O$: C, 68.4% H, 6.56% N, 18.38% and Found: C, 68.15% H, 6.68% N, 18.25%.

In the same manner but replacing chloroacetonitrile with an equivalent amount of ethyl bromoacetate, 2-phenoxyethyl bromide, 2-ethoxyethyl bromide, 2-(2-chloroethoxy)-ethanol, phenethyl bromide, 2-[4-(1,1-dimethylethyl)phenoxy]ethyl bromide, 2-(4-chlorophenoxy)ethyl bromide, 2-[4-(acetylamino)phenoxy]ethyl bromide, 2-(3-indolyl)ethyl bromide, 2-(1H-imidazol-4-yl)ethyl bromide or 1-(p-toluenesulfonyl)-2-(4-fluorophenyl)ethane, the following compounds of formula I were obtained respectively: 4-(2-oxo-3,5,7-cycloheptatrien-1-yl)-1-piperazine acetic acid, ethyl ester (Z)-2-butenedioate (I: Alk=$CH_2$, $R^1$=H and $R^2$=ethoxycarbonyl): mp 106°-116° C. (crystallized from acetone-diethyl ether); ir(mull) 2340, 1738, 1695 and 1553 $cm^{-1}$; uv max(MeOH) 344 ($\epsilon$=7630) and 251 nm($\epsilon$=12080); nmr(DMSO-$d_6$)$\delta$1.25 (t, 3H), 3.0 (m, 4H), 3.4 (m, 4H), 3.7 (s, 2H), 4.15 (q, 2H), 6.15 (s, 2h) and 6.9 (m, 5H); and Anal. Calcd for $C_{15}H_{20}N_2O_3$.$C_4H_4$-$O_4\frac{1}{2}H_2O$: C, 56.85% H, 6.28% N, 6.98% and Found: C, 56.52% H, 6.27% N, 6.74%; 2-[4-(2-phenoxyethyl)-1-piperazinyl]-2,4,6-cycloheptatrien-1-one (I: Alk=$CH_2CH_2$, $R^1$=H and $R^2$=phenoxy): mp 94°-95° C. (crystallized from ethyl acetate-diethyl ether); ir($CHCl_3$) 1565 $cm^{-1}$; uv max(MeOH) 351 ($\epsilon$=9840), 256 ($\epsilon$=15580) and 219 nm($\epsilon$=21075); nmr ($CDCl_3$) $\delta$2.75 (m, 6H), 3.35 (m, 4H), 4.10 (t, 2H) and 7.0 (m, 9H); and Anal. Calcd for $C_{19}H_{22}N_2O_2$: C, 73.52% H, 7.08% N, 9.02% and Found: C, 73.43% H, 7.16% N, 8.97%; 2-[4-(2-ethoxyethyl)-1-piperazinyl]-2,4,6-cycloheptatrien-1-one (I: Alk=$CH_2CH_2$, $R^1$=H and $R^2$=ethoxy): mp 137°-138° C. (crystallized from acetone-diethyl ether); ir($CHCl_3$) 2450, 1900 and 1705 $cm^{-1}$; uv max(meOH) 344 ($\epsilon$=9470) and 251 nm($\epsilon$=14940); nmr($CDCl_3$) $\delta$1.2 (t, 3H), 3.55 (m, 14H), 6.2 (s, 2H), 6.9 (m, 5H) and 13.3 (broad, 2H); and Anal. Calcd for $C_{15}H_{22}N_2O_2$.$C_4H_4O_4$: C, 60.30% H, 6.87% N, 7.40% and Found: C, 60.27% H, 6.89% N, 7.17%; 2-[4-[2-(2-hydroxyethoxy)ethyl]-1-piperazinyl]-2,4,6-cycloheptatrien-1-one (I: Alk=$CH_2CH_2$, $R^1$=H and $R^2$=2-hydroxyethoxy): ir($CHCl_3$) 3660, 3400, 1555 and 1612 $cm^{-1}$; uv max(MeOH) 351 ($\epsilon$=8825), 255

($\epsilon$=12810) and 222 nm($\epsilon$=10330); and nmr(CDCl$_3$) $\delta$2.65 (m, 6H), 3.34 (t, 4H), 3.60 (m, 6H) and 6.60-6.95 (m, 5H); 2-[4-(2-phenylethyl)-1-piperazinyl]-2,4,6-cycloheptatrien-1-one (I: Alk=CH$_2$CH$_2$, R$^1$=H and R$^2$=phenyl): ir(CHCL$_3$) 1365 cm$^{-1}$; uv max(MeOH) 255 nm($\epsilon$=12290) and nmr(CDCl$_3$)$\delta$2.75 (m, 8H), 3.35 (m, 4H) and 7.0 (m, 10H); 2-[4-[2-[4-(1,1-dimethylethyl)-phenoxy]ethyl]-1-piperazinyl]-2,4,6-cycloheptatrien-1-one (I: Alk=CH$_2$CH$_2$, R$^1$=H and R$^2$=4-(1,1-dimethylethyl)phenoxy): ir(CHCl$_3$) 1565 cm$^{-1}$; uv max(MeOH) 351 ($\epsilon$=9830), 256 ($\epsilon$=15290) and 223 nm($\epsilon$=22515); nmr(CDCl$_3$)$\delta$1.30 (s, 9H), 2.80 (m, 6H), 3.40 (m, 4H), 4.15 (t, 2H) and 7.00 (m, 9H); and Anal. Calcd for C$_{23}$H$_{30}$N$_2$O$_2$: C, 75.37% H, 8.25% N, 7.65% and Found: C, 75.07% H, 8.15% N, 7.67%; 2-[4-[2-(4-chlorophenoxy)ethyl]-1-piperazinyl]-2,4,6-cycloheptatrien-1-one (I: Alk=CH$_2$CH$_2$, R$^1$=H and R$^2$=4-chlorophenoxy): mp 89°-91° C. (crystallized from ethyl acetate); ir(CHCl$_3$) 1565 cm$^{-1}$; uv max(MeOH) 351 ($\epsilon$=9575), 255 ($\epsilon$=14625) and 227 nm ($\epsilon$=23650); nmr(CDCl$_3$)$\delta$2.80 (m, 6H), 3.40 (t, 4H), 4.10 (t, 2H) and 7.00 (m, 9H); and Anal. Calcd for C$_{19}$H$_{21}$ClN$_2$O$_2$: C, 66.17% H, 6.14% N, 8.12% and Found: C, 65.94% H, 6.13% N, 8.09%; 2-[4-[2-[4-(acetylamino)phenoxy]ethyl]-1-piperazinyl]-2,4,6-cycloheptatrien-1-one (I: Alk=CH$_2$CH$_2$, R$^1$=H and R$^2$=4-(acetylamino)phenoxy): mp 141°-143° C.; ir(CHCl$_3$) 3430, 3300, 1680 and 1560 cm$^{-1}$; uv max (MeOH) 351 ($\epsilon$=9990) and 252 nm($\epsilon$=30610); nmr(CDCl$_3$) $\delta$2.10 (s, 3H), 2.80 (m, 6H), 3.40 (t, 4H), 4.10 (t, 4H) and 7.00 (m, 9H); and Anal. Calcd for C$_{21}$H$_{25}$N$_3$O$_3$: C, 68.64% H, 6.86% N, 11.44% and Found: C, 68.48% H, 6.76% N, 11.31%; 2-[4-[2-(3-indolyl)ethyl]-1-piperazinyl]-2,4,6-cycloheptatrie-1-one (I: Alk=CH$_2$CH$_2$, R$^1$=H and R$^2$=3-indolyl): mp 128°-129° C. (crystallized from ethyl acetate-hexane); ir(mull) 3310 and 1555 cm$^{-1}$; uv max(MeOH) 352 ($\epsilon$=9700), 290 ($\epsilon$=8680), 257 ($\epsilon$=16960) and 222 nm($\epsilon$=46990); nmr(DMSO-d$_6$) $\delta$2.60 (m, 8H), 3.25 (m, 4H), 7.00 (m, 10H) and 10.2 (s, 1H); and Anal. Calcd for C$_{21}$H$_{23}$N$_3$O: C, 75.65% H, 6.95% N, 12.60% and Found: C, 75.53% H, 7.11% N, 12.47%; 2-[4-[2-(1H-imidazol-4-yl)ethyl]-1-piperazinyl]-2,4,6-cycloheptatrien-1-one (I: Alk=CH$_2$CH$_2$, R$^1$=H and R$^2$=1H-imidazol-4-yl): mp 139°-141° C. (crystallized from acetone-diethyl ether); ir(mull) 2800 and 1560 cm$^{-1}$; uv max(MeOH) 350 ($\epsilon$=9970) and 255 nm($\epsilon$=14915); nmr(CDCl$_3$) $\delta$2.57 (m, 8H), 3.40(m, 4H) and 7.00); and Anal. Calcd for C$_{16}$H$_{20}$N$_4$O: C, 67.58% H, 7.09% N, 19.71% and Found: C, 67.10% H, 7.09% N, 19.64%; and 2-[4-[2-(4-fluorophenyl)ethyl]-1-piperazinyl]-2,4,6-cycloheptatrien-1-one hydrochloride (I: Alk=CH$_2$CH$_2$, R$^1$=H and R$^2$=4-fluorophenyl): mp 208°-210° C.; ir(nujol) 2280 cm$^{-1}$; uv max(MeOH) 343 ($\epsilon$=9700), 251 ($\epsilon$=14315) and 222 nm ($\epsilon$=11555); nmr(DMSO-d$_6$)$\delta$3.4(m, 12H) and 7.1 (m, 9H); and Anal. Calcd for C$_{19}$H$_{21}$FN$_2$O: C, 65.40% H, 6.35% N, 8.06% and Found: C, 65.27% H, 6.37% N, 8.04%.

EXAMPLE 4

2-[4-[2-(3,4-Dimethoxyphenyl)ethyl]-1-piperazinyl]-2,4,6-cycloheptatrien-1-one (I: Alk=CH$_2$CH$_2$, R$^1$=H and R$^2$=3,4-dimethoxyphenyl)

To a solution of 3,4-dimethoxyphenethanol (4.4 g) in methylene chloride (15 ml) containing triethylamine (2.7 g or 3.7 ml), was added gradually a solution of tosyl chloride (5.07 g) in methylene chloride (15 ml). The mixture was stirred at room temperature overnight. The mixture was diluted with chloroform and washed with water. The organic layer was separated, dried and evaporated to yield a crude product (11.7 g). The product was passed through a column of silica gel (250 g) and the eluates were evaporated to give 3,4-dimethoxyphenethyl tosylate (7.2 g): ir(CHCl$_3$) 1600 and 1500 cm$^{-1}$; and nmr(CDCl$_3$) $\delta$2.4 (s, 3H), 2.85 (m, 2H), 3.72 (s, 3H), 3.75 (s, 3H), 4.15 (t, 2H), 6.6 (m, 2H), 7.23 (m, 3H) and 7.64 (m, 2H).

A mixture of the latter compound (15.4 g), 2-(1-piperazinyl)-2,4,6-cycloheptatrien-1-one acetate (10.4 g, described in Example 2) and potassium carbonate (12.54 g) in acetone (105 ml) was refluxed for 24 hr and evaporated. A solution of the residue in chloroform was washed with water, dried and evaporated. The residue was treated with a solution of hydrogen chloride in diethyl ether and the precipitate was collected and crystallized from methanol to obtain the hydrochloride salt (8.53 g) of the title compound, mp 175°-178° C. The latter salt (3.2 g) was dissolved in water and 10% sodium hydroxide was added until the solution was alkaline. After extraction with chloroform, the extract was dried, evaporated and crystallized from diethyl ether-hexane to obtain the title compound (2.0 g): mp 83°-85° C.; ir(CHCl$_3$) 1565, 1200 and 1145 cm$^{-1}$; uv max(MeOH) 350 ($\epsilon$=9860), 256 ($\epsilon$=15130) and 227 nm($\epsilon$=19500); nmr(CDCl$_3$)$\delta$2.7 (m, 2H), 3.4 (m, 4H), 3.85 (s, 6H) and 6.8 (m, 8H); and Anal. Calcd for C$_{21}$H$_{26}$N$_2$O$_3$: C, 71.16% H, 7.39% N, 7.91% and Found: C, 71.31% H, 7.62% N, 7.78%.

EXAMPLE 5

2-[4-[2-(3,4-Dihydroxyphenyl)ethyl]-1-piperazinyl]-2,4,6-cycloheptatrien-1-one (I: Alk=CH$_2$CH$_2$, R$^1$=H, and R$^2$=3,4-dihydroxyphenyl)

A solution of 2-[4-[2-(3,4-dimethoxyphenyl)ethyl]-1-piperazinyl]-2,4,6-cycloheptatrien-1-one (1.10 g, described in Example 4) in methylene chloride (5 ml) was cooled to −65° C. in dry ice bath. A solution of boron tribromide (3.36 g) in methylene chloride (5 ml) was added dropwise to the solution of the compound. After the addition, the temperature was allowed to rise to room temperature. After 4 hr, the mixture was cooled in an ice bath and methanol (20 ml) was added dropwise. The resulting mixture was slowly brought to reflux and the solid was allowed to dissolve. The solution was then concentrated to the point at which crystals start to separate. Some diethyl ether was added, the mixture was cooled overnight, and filtered to give crude product (1.4 g). Recrystallization form methanol gave the hydrobromide salt (0.5 g) of the title compound: mp 256°-258° C.; ir(nujol) 3490, 2540 and 1522 cm$^{-1}$; uv max(MeOH) 342 ($\epsilon$=7820), 250 ($\epsilon$=10720) and 222 nm($\epsilon$=11535); nmr(DMSO-d$_6$)$\delta$3.25 (m, 12H), 6.8 (m, 7H) and 8.7 (broad, 2H); and Anal. Calcd for C$_{19}$H$_{22}$N$_2$O$_3$.HBr: C, 56.02% H, 5.69% N, 6.88% and Found: C, 55.91% H, 5.74% N, 6.86%.

EXAMPLE 6

4-(2-Oxo-3,5,7-cycloheptatrien-1-yl)-1-piperazineacetamide (I: Alk=CH$_2$, R$^1$=H and R$^2$=aminocarbonyl)

A solution of 4-(2-oxo-3,5,7-cycloheptatrien-1-yl)-1-piperazine-acetonitrile (3.0 g; described in Example 3) in conc. sulfuric acid (30 ml) was allowed to stay at room temperature for 3 days. The reaction mixture was poured over ice and conc. ammonium hydroxide slowly while stirring, then extracted with chloroform. Evaporation of the solvent left 2.7 g crude product, which was recrystallized from methanol to yield 2.2 g of the title compound: mp 169°–171° C.; ir(CHCl3) 3500, 3430, 3370, 1685 and 1563 cm$^{-1}$; uv max(MeOH) 351 ($\epsilon$=9920), 254 ($\epsilon$=14810) and 221 nm($\epsilon$=12090); nmr(CDCl3)$\delta$2.75 (t, 4H), 3.09 (s, 2H), 3.35 (t, 4H), 6.00 (2H) and 6.8 (m, 5H); and Anal. Calcd for C13H17N3O2: C, 63.14% H, 6.93% N, 16.99% and Found: C, 63.24% H, 7.00% N, 16.99%.

EXAMPLE 7

2-[4-[2-(Acetyloxy)ethyl]-1-piperazinyl]-2,4,6-cycloheptatrien-1-one (I: Alk=CH2CH2, R$^1$=H and R$^2$=acetyloxy)

A mixture of 1-(2-hydroxyethyl)piperazine (10.0 g) and 2-methoxy-2,4,6-cycloheptatrien-1-one (10.9 g) in methanol (50 ml) was refluxed for 24 hr and evaporated. The residue was chromatographed on silica gel (100 g) using methanol-ethyl acetate (1:4). The eluates were evaporated and crystallized from ethyl acetate-hexane to give 4-(2-oxo-3,5,7-cycloheptatrien-1-yl)-1-piperazine-ethanol (9.2 g): mp 85°–86° C.; ir(CHCl3) 3440, 1616 and 1555 cm$^{-1}$; nmr(CDCl3) $\delta$2.55 (t, 2H), 2.63 (m, 4H), 3.30 (m, 4H), 3.60 (t, 2H) and 6.40–7.65 (m, 5H); and Anal. Calcd for C13H18N2O2: C, 66.64% H, 7.74% N, 11.96% and Found: C, 66.12% H, 7.83% N, 11.99%.

To a solution of the latter compound (0.70 g) in pyridine (5 ml), acetic anhydride (15 ml) was added and the reaction mixture was allowed to stay at room temperature for 16 hr and evaporated. The residue was chromatographed on 50 g of silica gel with methanol-ethyl acetate (20:80) to yield 950 mg of still impure product. It was rechromatographed on 100 g silica gel with methanol-ethyl acetate (5:95) to obtain 780 mg of the pure title compound as an oil: ir(CHCl3) 1730 and 1560 cm$^{-1}$; uv max(MeOH) 351 ($\epsilon$=9445) and 255 nm($\epsilon$=14240); and nmr(CDCl3)$\delta$2.08 (s, 3H), 2.7 (t, 6H), 3.35 (t, 4H), 4.2 (t, 2H) and 6.9 (m, 5H).

EXAMPLE 8

2,2-Dimethylpropanoic Acid, 2-[4-(2-Oxo-3,5,7-cycloheptatrien-1-yl)-1-piperazinyl]ethyl Ester (I: Alk=CH2CH2, R$^1$=H, and R$^2$=2,2-dimethyl-1-oxopropoxy)

To a solution of 4-(2-oxo-3,5,7-cycloheptatrien-1-yl)-1-piperazine-ethanol (7.04 g, described in Example 7) in methylene chloride (100 ml), triethylamine (4.3 g) was added followed by the dropwise addition of 2,2-dimethylpropanoyl chloride. The resulting solution was allowed to stay at room temperature for 3 days, then washed with water, dried over sodium sulfate and evaporated. The residue was chromatographed twice on 250 g of silica gel with ethyl acetate to yield 3.5 g of the title compound. The title compound (3.0 g) was dissolved in acetone (15 ml) and a solution of maleic acid (1.16 g) in acetone (15 ml) was added. Diethyl ether (100 ml) was added to give the (Z)-2-butenedioate salt (2.5 g) of the title compound; mp 101°–102° C.; ir(mull) 2350, 1723, 1700 and 1545 cm$^{-1}$; uv max(MeOH) 343 ($\epsilon$=8040) and 251 nm($\epsilon$=12645); nmr(DMSO-d6) $\delta$1.2 (m, 9H), 3.3 (m, 10H), 4.3 (m, 2H), 6.1 (s, 2H) and 6.95 (m, 5H); and Anal. Calcd for C18H26N2O3.C4H4O4: C, 60.82% H, 6.96% N, 6.45% and Found: C, 60.74% H, 7.01% N, 6.16%.

EXAMPLE 9

2-[4-[2-(Acetylthio)ethyl]-1-piperazinyl]-2,4,6-cycloheptatrien-1-one (I: Alk= CH2CH2, R$^1$=H and R$^2$=acetylthio)

A mixture of 4-(2-oxo-3,5,7-cycloheptatrien-1-yl)-1-piperazine-ethanol (10.0 g, described in Example 7), potassium carbonate (26 g) and chloroform (150 ml) was stirred and cooled in an ice-bath. Thionyl chloride (11.7 g) was added dropwise over a period of 30 min and allowed to react with stirring at room temperature for 16 hr. Water (50 ml) was added and extracted with chloroform. After drying over magnesium sulfate, the extract was evaporated and the residue (11.0 g) was chromatographed on 500 g silica gel with ethyl acetate to yield 6.2 g of 2-[4-(2-chloroethyl)-1-piperazinyl]-2,4,6-cycloheptatrien-1-one mp 71°–73° C.; ir(CHCl3) 1560 cm$^{-1}$; uv max(MeOH) 352 ($\epsilon$=9730) and 255 nm($\epsilon$=14300); nmr(CDCl3) $\delta$2.75 (m, 6H), 3.5 (m, 6H) and 7.0 (m, 5H) and Anal. Calcd for C13H17—ClN2O: C, 61.77% H, 6.78% N, 11.08% and Found: C, 61.60% H, 6.79% N, 10.98%.

A mixture of the latter compound (2.53 g), thiourea (800 mg) and ethanol (25 ml) was refluxed for 2 hr and evaporated. The residue was dissolved in water and washed with chloroform. The aqueous layer was freeze-dried to yield 3.06 of the hydrochloride salt of 2-[4-[2-[[(aminoiminomethyl)amino]thio]ethyl]-1-piperazinyl]-2,4,6-cycloheptatrien-1-one. A part of this salt (1.5 g) was stirred at 50° C. with 25 ml acetic anhydride for 45 min and cooled to room temperature. Methanol (10 ml) was added and the solution was evaporated to dryness in vacuo, to obtain 2.87 g of crude product. It was dissolved in ethyl acetate, washed first with 10% sodium hydroxide, then, with water, dried over sodium sulfate and evaporated to give a residue (1.2 g). This residue was chromatographed on silica gel using ethyl acetate to give the title compound (0.39 g): mp 75°–77° C.; ir(CHCl3) 1680, 1610 and 1560 cm$^{-1}$; uv max(MeOH) 351 ($\epsilon$=8960), 254 ($\epsilon$=13930) and 225 nm($\epsilon$=14100); nmr(CDCl3) $\delta$2.67 (m, 6H), 3.03 (t, 2H), 3.34 (t, 4H) and 6.60–7.20 (m, 5H); and Anal. Calcd for C15H20N2O2S: C, 61.63% H, 6.90% N, 9.58% and Found: C, 61.68%H, 6.95% N, 9.46%.

We claim:
1. A compound of the formula

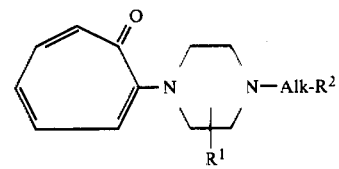

in which Alk is a divalent alkyl having one to six carbon atoms; R$^1$ is hydrogen or lower alkyl having one to three carbon atoms; and R$^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1-imidazol-4-yl, 1-oxo(lower)alkoxy, acetylthio, phenyl mono-, di or trisubstituted with lower alkyl, halo, lower alkoxy, hydroxy or trifluoromethyl, or phenoxy mono-, di- or trisubstituted with lower alkyl, halo, lower alkoxy, acetylamino, hydroxy or trifluoromethyl; or a therapeutically acceptable acid addition salt thereof.

2. A compound of claim 1 in which Alk is a divalent alkyl having one to six carbon atoms; $R^1$ is hydrogen; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkoxy or hydroxy, or phenyl mono-, di- or trisubstituted with lower alkyl, halo or acetylamino; or a therapeutically acceptable acid addition salt thereof.

3. A compound of claim 1 in which Alk is a divalent alkyl having one to three carbon atoms; $R^1$ is hydrogen; and $R^2$ is lower alkoxy, cyano, aminocarbonyl, lower alkoxycarbonyl cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono- or disubstituted with lower alkoxy or hydroxy, or phenoxy monosubstituted with lower alkyl, halo or acetylamino; or a therapeutically acceptable acid addition salt thereof.

4. A compound of claim 1 in which Alk is a divalent alkyl having one or two carbon atoms; $R^1$ is hydrogen; and $R^2$ is lower alkoxy, cyano, 1-oxo(lower)alkoxy, or phenyl mono- or disubstituted with lower alkoxy or hydroxy; or a therapeutically therapeutically acid addition salt thereof.

5. 2-[4-(Phenylmethyl)-1-piperazinyl]-2,4,6-cycloheptatrien-1-one, a compound of claim 1 wherein Alk is $CH_2$, $R^1$ is hydrogen and $R^2$ is phenyl.

6. N,4-Bis-(2-oxo-3,5,7-cycloheptatrien-1-yl)-1-piperazine-ethanamine, a compound of claim 1 wherein Alk is $CH_2CH_2$, $R^1$ is hydrogen and $R^2$ is 1-oxo-2,4,6-cycloheptatrien-2-ylamino.

7. 4-(2-Oxo-3,5,7-cycloheptatrien-1-yl)-1-piperazine acetic acid, ethyl ester, a compund of claim 1 wherein Alk is $CH_2CH_2$, $R^1$ is hydrogen and $R^2$ is ethoxycarbonyl.

8. 4-(2-Oxo-3,5,7-cycloheptatrien-1-yl)-1-piperazine-acetonitrile, a compound of claim 1 wherein Alk is $CH_2$, $R^1$ is hydrogen and $R^2$ is cyano.

9. 2-[4-(2-(Phenoxyethyl)-1-piperazinyl]-2,4,6-cycloheptatrien-1-one, a compound of claim 1 wherein Alk is $CH_2Ch_2$, $R^1$ is hydrogen and $R^2$ is phenoxy.

10. 2-[4-(2-Ethoxyethyl)-1-piperazinyl]-2,4,6-cycloheptatrien-1-one, a compound of claim 1 wherein Alk is $CH_2CH_2$, $R^1$ is hydrogen and $R^2$ is ethoxy.

11. 2-[4-[2-(2-Hydroxyethoxy)ethyl]-1-piperazinyl]-2,4,6-cycloheptatrien-1-one, a compound of claim 1 wherein Alk is $CH_2CH_2$, $R^1$ is hydrogen and $R^2$ is 2-hydroxyethoxy.

12. 2-[4-(2-phenylethyl)-1-piperazinyl]-2,4,6-cycloheptatrien-1-one, a compound of claim 1 wherein Alk is $CH_2CH_2$, $R^1$ is hydrogen and $R^2$ is phenyl.

13. 2-[4-[2-(3,4-Dimethoxyphenyl)ethyl]-1-piperazinyl]-2,4,6-cycloheptatrien-1-one, a compound of claim 1 wherein Alk is $CH_2CH_2$, $R^1$ is hydrogen and $R^2$ is 3,4-dimethoxyphenyl.

14. 2-[4-[2-(3,4-Dihydroxyphenyl)ethyl]-1-piperazinyl]-2,4,6-cycloheptatrien-1-one, a compound of claim 1 wherein Alk is $CH_2CH_2$, $R^1$ is hydrogen and $R^2$ is 3,4-dihydroxyphenyl.

15. 4-(2-Oxo-3,5,7-cycloheptatrien-1-yl)-1-piperazine-acetamide, a compound of claim 1 wherein Alk is $CH_2CH_2$, $R^1$ is hydrogen and $R^2$ is aminocarbonyl.

16. 2-[4-[2-(Acetyloxy)ethyl]-1-piperazinyl]-2,4,6-cycloheptatrien-1-one, a compound of claim 1 wherein Alk is $CH_2CH_2$, $R^1$ is hydrogen and $R^2$ is acetyloxy.

17. 2,2-Dimethylpropanoic acid, 2-[4-(2-oxo-3,5,7-cycloheptatrien-1-yl)-1-piperazinyl]ethyl ester, a compound of claim 1 wherein Alk is $CH_2CH_2$, $R^1$ is hydrogen and $R^2$ is 2,2-dimethyl-1-oxopropoxy.

18. 2-[4-[2-[4-(1,1-Dimethylethyl)phenoxy]ethyl]-1-piperazinyl]-2,4,6-cycloheptatrien-1-one, a compound of claim 1 wherein Alk is $CH_2CH_2$, $R^1$ is hydrogen and $R^2$ is 4-(1,1-dimethylethyl)phenoxy.

19. 2-[4-[2-(4-Chlorophenoxy)ethyl]-1-piperazinyl]-2,4,6-cycloheptatrien-1-one, a compound of claim 1 wherein Alk is $CH_2CH_2$, $R^1$ is hydrogen and $R^2$ is 4-chlorophenoxy.

20. 2-[4-[2-[4-(Acetylamino)phenoxy]ethyl]-1-piperazinyl]-2,4,6-cycloheptatrien-1-one, a compound of claim 1 wherein Alk is $CH_2CH_2$, $R^1$ is hydrogen and $R^2$ is 4-acetylamino)phenoxy).

21. 2-[4-[2-(3-Indolyl)ethyl]-1-piperazinyl]-2,4,6-cycloheptatrien-1-one, a compound of claim 1 wherein Alk is $CH_2CH_2$, $R^1$ is hydrogen and $R^2$ is 3-indolyl.

22. 2-[4-[2-(1H-Imidazol-4-yl)ethyl]-1-piperazinyl]-2,4,6-cycloheptatrien-1-one, a compound of claim 1 wherein Alk is $CH_2CH_2$, $R^1$ is hydrogen and $R^2$ is 1H-imidazol-4-yl.

23. 2-[4-[2-(Acetylthio)ethyl]-1-piperazinyl]-2,4,6-cycloheptatrien-1-one, a compound of claim 1 wherein Alk is $CH_2CH_2$, $R^1$ is hydrogen and $R^2$ is acetylthio.

24. 2-[4-[2-(4-Fluorophenyl)ethyl]-1-piperazinyl]-2,4,6-cycloheptatrien-1-one, a compound of claim 1 wherein Alk is $CH_2CH_2$, $R^1$ is hydrogen and $R^2$ is 4-fluorophenyl.

25. A pharmaceutical composition, for stimulating dopamine receptors in a mammal in need thereof, which comprises an effective dopamine receptor stimulating amount of a compound of the formula

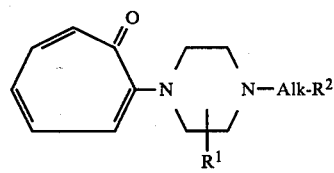

in which Alk is a divalent alkyl having one to six carbon atoms; $R^1$ is hydrogen or lower alkyl having one to three carbon atoms; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkyl, halo, lower alkoxy, hydroxy or trifluoromethyl, or phenyl mono-, di- or trisubstituted with lower alkyl, halo, lower alkoxy, acetylamino, hydroxy or trifluoromethyl; or a therapeutically acceptable acid addition salt thereof, and a pharmaceutically acceptable carrier therefor.

26. A method of stimulating dopamine receptors in a mammal in need thereof, which comprises administering to said mammal and effective dopamine receptor stimulating amount of a composition of claim 25.

27. A method of stimulating dopamine receptors in a mammal in need thereof, which comprises administering to said mammal an effective dopamine receptor stimulating amount of a composition of claim 25, in combination with an effective amount of an agent selected from bromocriptine, lergotrile, levodopa, combination of levodopa and carbidopa, L-prolyl-L-leucylglycinamide and L-prolyl-N-methyl-D-leucylglycinamide.

28. The method of claim 27 wherein the composition of claim 25, and said agent are administered sequentially or simultaneously.

29. A pharmaceutical composition for stimulating dopamine receptors in a mammal in need thereof comprising an effective dopamine receptor stimulating amount of a compound of the formula

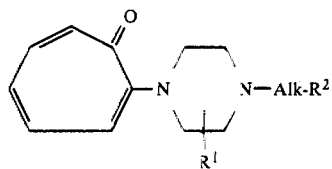

in which Alk is a divalent alkyl having one to six carbon atoms; $R^1$ is hydrogen or lower alkyl having one to three carbon atoms; and $R^2$ is lower alkoxy, cyano, aminocarbonyl, lower alkoxycarbonyl, cyclo(lower)alkyl, phenyl, phenoxy, hydroxy(lower)alkoxy, 3-indolyl, 1-oxo-2,4,6-cycloheptatrien-2-yl-amino, 1H-imidazol-4-yl, 1-oxo(lower)alkoxy, acetylthio, phenyl mono-, di- or trisubstituted with lower alkyl, halo, lower alkoxy, hydroxy or trifluoromethyl, or phenoxy mono-, di- or trisubstituted with lower alkyl, halo, lower alkoxy, acetylamino, hydroxy or trifluoromethyl; or a therapeutically acceptable acid addition salt thereof, and an agent selected from bromocriptine, lergotrile, levodopa, combination of levodopa and carbidopa, L-propyl-L-leucylglycinamide and L-propyl-N-methyl-D-leucylglycinamide.

* * * * *